United States Patent [19]

Ghelli et al.

[11] 4,419,515

[45] Dec. 6, 1983

[54] TWO STAGE PROCESS FOR PREPARING 2,6-PYRIDINEDICARBOXYLIC ACID

[75] Inventors: Giovanni Ghelli, Savona; Enrico Bruschi; Gino Agnese, both of Genoa, all of Italy

[73] Assignee: Luigi Stoppani S.p.A., Milan, Italy

[21] Appl. No.: 283,082

[22] Filed: Jul. 13, 1981

Related U.S. Application Data

[63] Continuation of Ser. No. 167,222, Jul. 9, 1980, abandoned, which is a continuation of Ser. No. 965,037, Nov. 30, 1978, Pat. No. 4,237,301.

[30] Foreign Application Priority Data

Dec. 1, 1977 [IT] Italy .............................. 30273 A/77

[51] Int. Cl.$^3$ ..................... C07F 11/00; C07D 213/55
[52] U.S. Cl. ........................................... 546/5; 546/2; 546/327
[58] Field of Search ................................ 546/2, 5, 327

[56] References Cited

U.S. PATENT DOCUMENTS 4,237,301 12/1980 Ghelli et al. ......................... 546/327

OTHER PUBLICATIONS

Epstein, Liebig's Ann. d. Chem., 231 (1895), pp. 24–36.
Ladenburg, Liebig's Ann. d. Chem., 247, (1888), pp. 32–41.
Black et al., Journ. Org. Chem., 14 (1949), p. 14.
Soine et al., Journal Ann. Pharm. Ass., 39, (195), p. 421.
Henge, Ber., 67, B (1934), pp. 750-753.
Hodson et al, Jr. Bacteriol., 91(2), (1966), pp. 562-569.
Ghelli et al., Chem. Abstracts, vol. 91, No. 19, 157, 616g, (Nov. 5, 1979), Abstracting Spanish Patent Specification 475546 Pub. 01 Apr. 1979.

Primary Examiner—Alan L. Rotman
Attorney, Agent, or Firm—Fleit, Jacobson, Cohn & Price

[57] ABSTRACT

This invention relates to a two stage process for preparing 2,6-pyridinedicarboxylic acid or dipicolinic acid from 2,6-dimethyl-pyridine through oxidation of the latter in an acid environment with hexavalent chromium salts and formation of a molar addition compound between dicarboxylic acid, being formed by oxidation, and chromic anhydride in the first stage, and subsequent hot hydrolysis of the addition product so obtained, thus isolating 2,6-pyridinedicarboxylic acid therefrom in the second stage. The invention also comprises the above mentioned intermediate complex addition compound and the 2,6-pyridinedicarboxylic acid of high purity, obtained by the process according to said invention.

7 Claims, 1 Drawing Figure

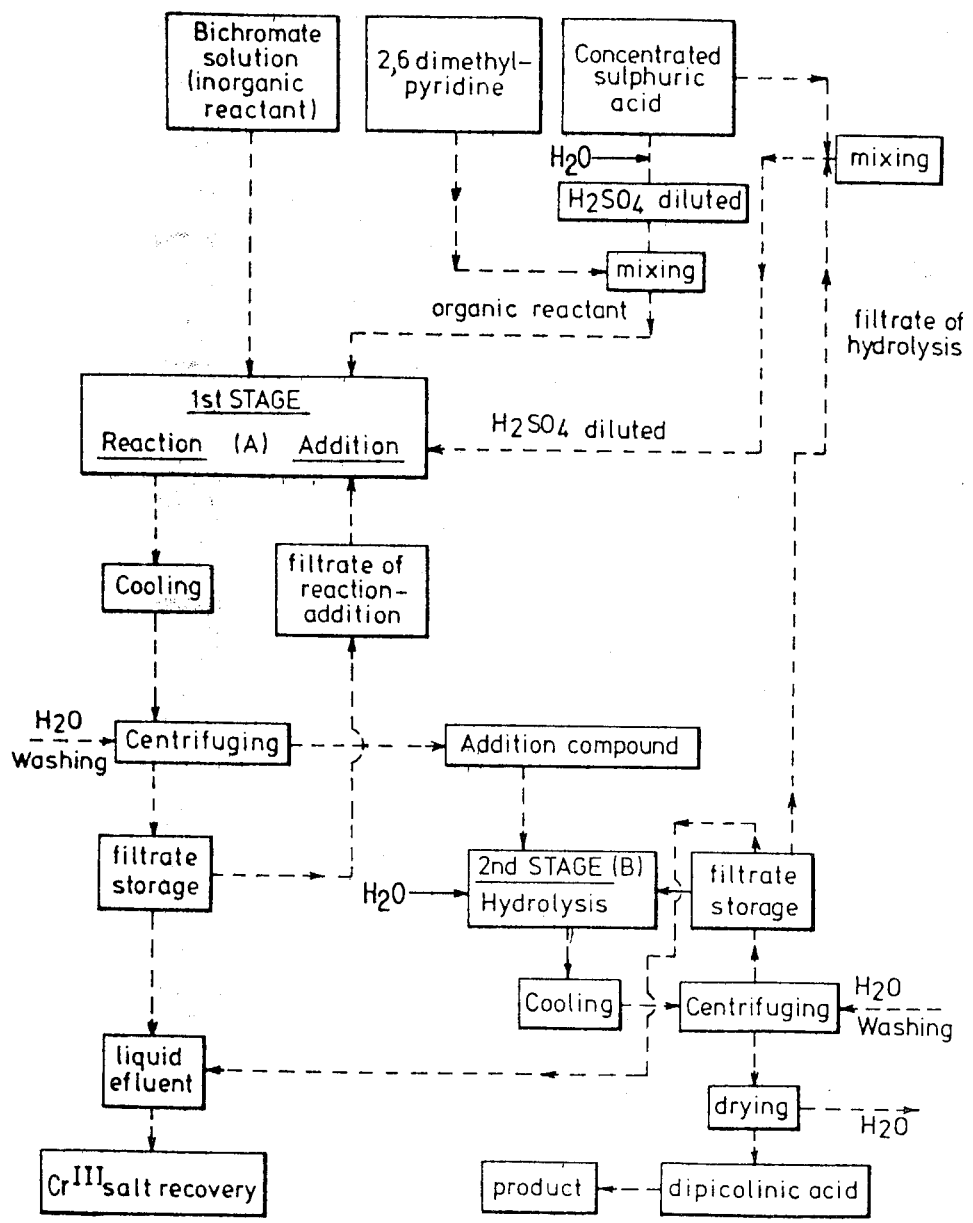

TWO STAGE PROCESS FOR PREPARING 2,6-PYRIDINEDICARBOXYLIC ACID

This application is a continuation of Ser. No. 167,222, filed on July 9, 1980, now abandoned, which is a continuation of Ser. No. 965,037, filed Nov. 30, 1978 now U.S. Pat. No. 4,237,301.

This invention relates to a two stage process for preparing 2,6-pyridine-dicarboxylic acid or dipicolinic acid from 2,6-dimethyl-pyridine through oxidation of the latter in an acidic environment with hexavalent chromium salts and formation of a molar addition compound between dicarboxylic acid, being formed by oxidation, and chromic anhydride in the first stage, and subsequent hot hydrolysis of the addition product so obtained, thus isolating 2,6-pyridine-dicarboxylic acid therefrom in the second stage.

The invention also comprises the above mentioned intermediate complex addition compound.

The invention also relates to 2,6-pyridine-dicarboxylic acid of high purity, obtained by the process according to the present invention.

For preparing 2,6-pyridine-dicarboxylic acid, more shortly referred to as dipicolinic acid, various processes have been already known, which may be summarized as follows:

(a) processes wherein 2,6-dimethyl-pyridine is oxidized with potassium permanganate (as to these processes particularly refer to):
(1) W. EPSTEIN; Liebig's Ann. d. Chem.; 231, 24 (1885);
(2) LADENBURG; Liebig's Ann. d. Chem.; 247, 32 (1888);
(3) G. BLACK E. DEPP. B. B. CORSON; Journ. Org. Chem.; 14, 14 (1949);
(4) T. O. SOINE, M. R. BUCHDAHL; Journ. Ann. Pharm. Ass.; 39, 421 (1950);
(5) U.S. Pat. No. 2,578,672; Dec. 18 (1951).
(b) Processes wherein 2,6-dimethyl-pyridine is oxidized with selenium dioxide, particularly disclosed in:
(6) HENZE; Ber.; 67, B, 750 (1934);
(7) German Ols No. 1,620,174; Apr. 27, 1972;
(c) processes based on biosynthesis through bacterium or bacterial cultures, particularly disclosed in:
(8) P. H. HODSON, J. W. Foster; J. Bacteriol.; 91(2)562, (1966);
(9) Japanese Pat. No. 14,394 (63); Sept. 21, (1961);
(10) U.S. Pat. No. 3,334,021; Aug. 1, (1967);
(11) German Ols No. 2,300,056; July 4, 1974.

(a) The processes of the first group all provide a total yield between 45 and 50%, and require a sequence of purifying operations, in any case leading to a dipicolinic acid, which may be still contaminated with mono-potassium salt and potassium chloride. Moreover, due to long reaction times (17-24 hours) and peculiar characteristics of the process, they have a maximum value of 2 in the ratio (in kg/cu.m. hour):

$$\frac{\text{amount of product}}{\text{volume unit} \times \text{time unit}}$$

which ratio represents a specific potential production and is of significance when designing an industrial production plant.

(b) The processes of the second group provide maximum total yields of 57%, require a sequence of highly complicated purifying operations and use a very valuable oxidizing means (SeO$_2$). From the available information, values of specific production cannot be drawn.

(c) In this third group very delicate processes are dealt with, characterized by the requirement of maintaining operative conditions, such as pH, temperature, saline concentration, that should be strictly controlled and have a very low value of specific production (such as, for example, a value of 5-6 kg/cu.m. culture/day). Efficiency information as homogeneous with those of chemical processes in oxidizing 2,6-dimethyl-pyridine cannot be provided, particularly due to the difference in the starting materials.

It will be appreciated that the hitherto used processes suffer from various disadvantages, particularly:
very low yield, reaching at the most 50% with permanganate processes and 57% with processes using SeO$_2$;
complicated systems or plants;
impurities included in the product, also because they are not removed by a simple recrystallization operation from water;
loss of reactants (which are not reprocessed or recycled).

On the other hand, a process according to the present invention has many advantages, which may be summarized as follows:
high rate of selectivity and complete conversion of raw material and accordingly a total yield exceeding 80%, up to 85% and even 90% in a continuous process;
high rate of specific production, at least 5 times higher than that found in conventional processes; this involves reduced plant sizes at the same production;
particularly high purity of the dipicolinic acid being produced which by simple recrystallization from water arrives at 99.9%;
simplicity of process layout as to both number of required operations and type of operations to be carried out;
possibility of recovery of chromium, which is at a trivalent state and in a form that can be intended for use in the leather tanning industry.

The product (dipicolinic acid) being obtained is per se of a high commercial interest, particularly for its high purity, as well as for its properties of dicarboxylic and heterocyclic organic acid capable of forming esters, amides and various other derivatives, therefore being very suitable for use as raw material for organic syntheses of different kinds, even very specialized.

Among various particularly interesting uses of this product are:
a monomer in the synthesis of polyester or polyamide type of copolymers; a stabilizing agent for peroxides and peracids, for example t-butyl peroxide, dimethyl-cyclohexanon peroxide, peroxyacetic acid and peroxy-monosulphuric acid; ingredient for polishing solution of metal surfaces; stabilizing agent for organic materials susceptible to be deteriorated due to the presence of traces of metal ions (sequestrating effect); stabilizing agent for epoxy resins; stabilizing agent for photographic solutions or emulsions (preventing the precipitation of calcium salts).

Prior to disclosing in detail the course of the dipicolinic acid making process, we deem it convenient to state hereinafter in advance some theoretical consideration relating to oxidation and addition reactions and hydrolysis reactions occurring in the first and second stages, respectively.

To this end, let us consider a specific example, wherein the oxidizer for hexavalent chromium is sodium bichromate, the acidificant agent is sulphuric acid and the compound to be oxidized is 2,6-dimethyl-pyridine. The advantage is gained by using such reactants that a solution of sodium and chromium sulphate is obtained as a filtering liquid in the first stage and the possibility of easily recovering in the second stage a pyridin-2,6-dicarboxylic acid of recovering in the second stage a pyridin-2,6-dicarboxylic acid of high purity, while recovering in the filtrate the trivalent chromium (as a complex salt), in a form that can be intended for use in the leather tanning industry, and accordingly as a valuable by-product, because of representing a saving in the total process.

The reactions occurring in the process according to the present invention may be summarized in the following molar schemes:

1st STAGE of oxidation and formation of the addition compound

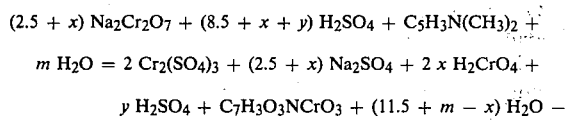

2nd STAGE of hydrolysis of the addition compound formed in the first stage:

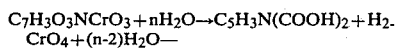

wherein x, y, m and n respectively represent:

x the excess bichromate moles relative to the equivalent stoichiometrical amount (2.5 moles) required by one mole of lutidine or 2,6-dimethyl-pyridine for the oxidation and addition reaction (mole/mole), leading to the formation of the addition compound between dipicolinic acid and chromic anhydride with removal of one molecule of water; index x varies between 0.25 and 2.50, values representing an excess of 10 and 100%, respectively, the preferred variation field or range being between 0.5 and 1.0, corresponding to an excess of 20 and 50%, respectively.

y, the moles of free acid per mole of complexed dipicolinic acid from $CrO_3$ formed; y varies between 3 and 20, preferably between 6 and 10;

m, represents the water moles at the beginning of the reaction; as it will be better explained in the following, this index varies in accordance with the ranges or concentration selected for the reactants, between 30 and 250, preferably between 40 and 150;

n, represents the water moles in the hydrolysis reaction (of the second stage) for one mole of the addition compound formed by dipicolinic acid $CrO_3$. As it will be better explained in the following, it varies in accordance with the weight ratio selected between complex salt and water in the range of 75-225, preferably between 135 and 165.

As previously noted, the oxidation of methyl groups of 2,6-dimethyl-pyridine is carried out in an acidic environment, under particular conditions later specified, with hexavalent chromium salts, soluble in water, such as alkaline bichromates (sodium, potassium, lithium, preferably sodium), or also with chromic anhydride, using sulphuric acid as an acidfying agent.

Substantially, the process is carried out with excess proportions of the oxidizer in solution with respect to the equivalent stoichiometrical value required by lutidine, as such conditions are the optimum conditions for the formation and isolation of the addition compound between dipicolinic acid and $CrO_3$, formation of which is essential and characterizing for the isolation of dipicolinic acid. This addition product is a novel product and it is intended to be claimed in the present invention.

This intermediate addition compound, then separated by filtering, appears as a crystalline solid and in the second stage is subjected to hydrolysis with water. Thus, 2,6-pyridine-dicarboxylic acid is obtained, which is isolated by filtering, washing and recrystallization from water, by which it can be obtained at an extremely high grade of purity, thereby being of particular value and interest for the intended uses.

The process, which may be carried out as a batch process or semi-continuous and even continuous process, enables total yields, calculated on the theoretical value obtainable in connection with 2,6-dimethyl-pyridine used, of higher than 80%, and up to 90%, where a continuous process is used.

BRIEF DESCRIPTION OF THE DRAWINGS

The sole FIGURE is a flow chart which illustrates an embodiment of the process in accordance with the present invention.

This process will now be described as a batch process according to the present invention in its details of practical embodiment, the disclosure being illustrated by the flow chart of the plant as shown in the FIGURE.

FIRST STAGE OF REACTION-ADDITION (A)

The reaction occurring in homogeneous phase is carried out between a solution of 2,6-dimethyl-pyridine in sulphuric acid, having a concentration of 50–80% by weight (preferably between 60 and 70%), and a solution of sodium bichromate having a concentration (expressed as $CrO_3$) of 40–65% by weight (preferably 45–50% by weight).

As above pointed out, bichromate is in excess relative to the stoichiometric amount required by lutidine for the formation of the addition compound mole/mole of dipicolinic acid with chromic anhydride. Such an excess is the range of 10–100% (preferably 20–50%).

In the case of a batch process, as that herein disclosed, the operation is carried out by gradually introducing the two reactants, organic (of lutidine sulphuric solution) and inorganic (bichromate solution) into a vessel of anticorrosive material (preferably enameled) under stirring and already containing the so-called "initial reaction foot," comprising 20–50% (preferably 35–45%) total sulphuric acid at the designed concentration and 10–40% (preferably 15–25%) total filtrate as recycled from filtering of the final reaction mass of a previous operation.

Such an operation mode proved to be necessary in practice, in case of batch and semicontinuous processes, to avoid a too violent reaction as the two reactants are introduced.

This "moderating" function of the "reaction foot" is not required in a continuous type of process, as being provided by the mass in the reaction during all of the reactant introducing steps.

The reaction in A is carried out at a temperature of 70°–115° C. (preferably 80°–110° C.) and takes a total time of 2–3 hours (initial period) for the introduction of the reactants, plus 3–0.5 hours (preferably 2–1 hours) for the actual reaction (time varying in accordance with temperature). Thus, a complete conversion of lutidine is obtained.

Whereupon, the mass obtained is cooled down to room temperature and the mass is filtered, thereby obtaining the separation of a liquid comprising a solution (aqueous solution) of chromium and sodium sulphate, also having therein the excess (relative to stoichiometrical) of introduced sulphuric acid and bichromate, and an orange-red crystalline solid which is washed and dried and has the following percent analytic composition:

| Found | Theoretical |
|---|---|
| Cr = 20.66% | Cr = 20.88% |
| N = 5.56% | N = 5.62% |
| C = 33.72% | C = 33.73% |
| H = 1.19% | H = 1.20% |
| O = 38.87% | O = 38.57% | and since by hydrolysis 67.1 parts by weight of dipicolinic acid and 40.2 parts by weight of $CrO_3$ are isolated from 100 parts by weight, it is deduced that the addition compound has the following general formula:

$$C_7H_3O_3N \cdot CrO_3$$

This addition compound is not described in the literature.

SECOND STAGE OF HYDROLYSIS (B)

Such as discharged from the centrifuge, the addition compound is supplied to the second stage, where it is treated with water at a ratio of water and solid (considered as dried) in the range of 5 and 15 (preferably in the range of 9 and 11), at 100°–50° C. (preferably at 100°–80° C.) for 0.5–4 hours (preferably 1–2 hours). By cooling to room (temperature preferably the range of 0°–15° C.), crystallized dipicolinic acid is obtained without crystallization water, which is then filtered, washed, and dried.

The product so obtained has a titer of 99.5%±0.2, m.p. 253±1° C. and has the following analytic data:

| | Found | Theoretical |
|---|---|---|
| N | 8.38% | 8.38% |
| C | 50.30% | 50.37% |
| H | 2.99% | 3.04% |
| O | 38.33% | 38.21% |

Total yield of the process as calculated on 2,6-dimethyl-pyridine: 80–90%.

The filtrate of dipicolinic acid is partly recycled to the hydrolysis reaction, partly to the preparing of diluted sulphuric acid which is for the reaction of the first stage, and partly is supplied to the liquid effluent for the recovery of chromium salts.

It is important in the hydrolysis stage to maintain the concentration of $CrO_3$ in the hydrolysis liquids below 6–7% (preferably 4%) by weight, by suitably adjusting the amount of filtrate from the centrifuge and hence the amount of water inroduced into the hydrolysis reaction and washing, to avoid to provide a product contaminated with chromium.

Some examples will now be given to illustrate the present invention, examples that in any case should not be considered as a limitation to the invention.

EXAMPLE 1

A universal type of laboratory reactor equipped with a stirrer was charged with 400 g 65% sulphuric acid by weight, with 370 g aqueous solution comprising 80 g chromium sulphate, 40 g sodium sulphate, 130 g 65% sulphuric acid by weight, 20 g chromic anhydride and 100 g water.

The mixture was heated to 90° C., while introducing in the same period of 2.5 hours, respectively:
  650 g of an aqueous solution of sodium bichromate, having a concentration in chromic anhydride of 46.5% by weight (450 g sodium bichromate crystallized with two molecules water, dissolved in 200 g water).
  525 g 65% sulphuric acid by weight containing 53.5 g dissolved of 2,6-dimethyl-pyridine.

The temperature was set to about 100° C. and, following introduction of the reactants, the reaction was continued for one hour at the same temperature.

After the fixed time of 3.5 hours, the mixture was cooled by stirring to about 25° C. and filtered, obtaining after washing with water an orange-red crystalline solid (dry weight 96 g) which was dispersed in 1200 g water and heated at 100° C. for one hour.

The product was cooled to about 20° C., filtered, washed and dried, obtaining 65 g crystalline white product which by analysis was 2,6-pyridine-dicarboxylic acid (titer 99.7%).

EXAMPLE 2

The reactor described in Example 1 was charged with 420 g liquid filtered from the reaction mass of Example 1 and 560 g 65% sulphuric acid.

Then, in a time of 3 hours and maintaining the temperature of 105° C., the reactor was charged, respectively, with:
  777 g aqueous solution of sodium bichromate at a concentration of 45.0% chromic anhydride by weight;
  990 g 67.2% sulphuric acid by weight, containing in solution 37.5 g 2,6-dimethyl-pyridine.

The reaction was continued for one hour at the same temperature and, after cooling, the mixture was filtered and washed, and an orange-red crystalline solid (dry weight 80 g) was isolated.

This solid was dispersed in 800 g water, heated for one hour at 90° C. and, after cooling, filtering and washing, 48 g 2,6-pyridin-dicarboxylic acid (titer 99.8%) was obtained.

EXAMPLE 3

The reactor described in the preceding examples was charged with 370 g liquid filtered from the reaction masses of the preceding examples and 400 g 65% sulphuric acid by weight.

The mass heated at 100° C. was then charged in a time of 2 hours with:
  650 g aqueous solution of 50% chromic anhydride by weight (325 g solid chromic anhydride dissolved in 325 g water); and 775 g 61.2% sulphuric acid by weight containing 53.5 g 2,6-dimethyl-pyridine by solution.

The reaction was continued for one hour at 100° C. and, after cooling the reacted mass to 20° C., the product was filtered and, after washing with water, an orange-red crystalline solid was obtained (dry weight 116 g).

The solid was dispersed in water (1200 g), then heating for one hour to 100° C., cooling, filtering and washing with water, thus isolating a white crystalline solid which, after drying, weighed 72 g and comprised 2,6-pyridine-dicarboxylic acid (titer 99.7%).

EXAMPLE 4

A universal type of pilot reactor was charged with 10.0 kg 65% sulphuric acid by weight, and 9.3 kg of a mixture of filtrates from the same type of preceding reactions carried out on laboratory scale.

The resulting mass was heated under stirring to 95° C. and the reactor was in the period of 2.5 hours simultaneously supplied with the two reactants (organic and inorganic), respectively consisting of:

organic reactant: 1.34 kg 2,6-dimethyl-pyridine, titer 98%, dissolved in 18.25 kg 65% sulphuric acid by weight;

inorganic reactant: 17.38 kg aqueous solution of sodium bichromate, prepared to contain 8.17 kg chromic anhydride.

At the end of the reactant supply, carried out at a temperature maintained in the range of 100°–115° C., the reaction was continued still under stirring for one further hour at about 115° C. At the end of the reaction, 2.5 liters water were evaporated. Under stirring, the product was cooled down to room temperature, the reacted mass was filtered, the solid was washed with 2 liters water and an orange-red crystalline product was obtained, weighing 2.96 kg (corresponding to 2.82 kg dried), and 33.5 liters filtrate (52.81 kg by weight).

The orange-red crystalline solid was dispersed in 27 liters boiling water and kept at 100° C. for one hour. The resulting solution was cooled down to room temperature, thus crystallizing 2,6-pyridine-dicarboxylic acid, which was filtered and washed. After drying, 1.72 kg product of titer 99.1% were obtained, which titer rose to 99.8% by recrystallization from water.

Total yield, calculated on 2,6-dimethyl-pyridine: 83%.

What is claimed is:

1. An intermediate molar addition compound prepared by oxidation of 2,6-dimethyl-pyridine, the process comprising the step of reacting at a temperature of from about 70°–115° C. and at atmospheric pressure in a homogeneous phase an acid solution of 2,6-dimethyl-pyridine with a solution of a soluble salt of hexavalent chromium having a concentration based on $CrO_3$ to provide from about a 10–100% stiochiometric excess to form said addition compound in insoluble form, and recovering said addition compound.

2. An intermediate molar addition compound prepared by oxidation of 2,6-dimethyl-pyridine, the process comprising the step of providing a first reactant which is a solution of 2,6-dimethyl-pyridine in about 50–80% by weight sulphuric acid so that after oxidation from about 3–20 moles of free acid per mole of 2,6-pyridinedicarboxylic acid are formed, providing a second reactant which is a solution of a soluble salt of hexavalent chromium having a concentration based on $CrO_3$ of from about 40–65% by weight to provide from about a 10–100% stoichiometric excess, reacting te two reactants in a homogeneous phase at a temperature of from about 70°–115° C. by gradually introducing the two reactants into an initial reaction foot during an initial introduction time of from about 2–3 hours and then allowing the reaction to continue for from about 3–0.5 hours whereby said intermediate molar addition compound is formed between 2,6-pyridinedicarboxylic acid and chromic anhydride with the removal of one molecule of water, cooling and separating said addition compound.

3. The addition compound of claim 2, wherein the initial reaction foot comprises from about 20–50% sulphuric acid and from about 10–40% of filtrate derived during the separation of 2,6-pyridinedicarboxylic acid in a second stage, the second stage comprising hydrolyzing said separated addition compound at a temperature of from about 100°–50° C. with water in an amount of from about 5–15 times the weight of the dry intermediate compound for from about 0.5–4 hours, the concentration of $CrO_3$ in the hydrolysis solution not exceeding about 7% by weight, cooling to precipitate said 2,6-pyridinedicarboxylic acid, and separating the precipitate from the hydrolysis solution.

4. The addition compound of claim 2, wherein the reaction temperature is from about 80°–110° C. the concentration of sulphuric acid is from about 60–70%, from about 6–10 moles (per mole of dipicolinic acid) of free acid are formed, the concentration of the soluble salt of hexavalent chromium based on $CrO_3$ is from about 45–50%, the stiochiometric excess of the oxidizing chromium salt is from about 20–50%, and the initial introduction time is from about 1–2 hours.

5. The addition compound of claim 4, wherein the initial reaction foot comprises from about 35–45% sulphuric acid and from about 15–25% of filtrate obtained during the separation of 2,6-pyridinedicarboxylic acid in a second stage, the second stage comprising hydrolyzing said separated addition compound at a temperature of from about 100°–50° C. with water in an amount of from about 5–15 times the weight of the dry intermediate compound for from about 0.5–4 hours, the concentration of $CrO_3$ in the hydrolysis solution not exceeding about 7% by weight, cooling to precipitate said 2,6-pyridinedicarboxylic acid, and separating the precipitate from the hydrolysis solution.

6. The addition compound of claim 2, wherein from about 30–250 moles of water per mole of 2,6-dimethyl-pyridine are present.

7. The addition compound of claims 1, 2, 3, 4, 5 or 6 which is an orange-red crystalline solid having the formula $C_7H_3O_3N \cdot CrO_3$ and an elementary composition as follows:

|    | Found  | Theoretical |
|----|--------|-------------|
| Cr | 20.66% | 20.88%      |
| N  | 5.56%  | 5.62%       |
| C  | 33.72% | 33.73%      |
| H  | 1.19%  | 1.20%       |
| O  | 38.87% | 38.57%      |

* * * * *